United States Patent
Brahler

[11] Patent Number: 6,089,866
[45] Date of Patent: *Jul. 18, 2000

[54] DRIVE SHAFT RETENTION MEANS FOR PROPHY ANGLE

[75] Inventor: George R. Brahler, Lawrence, Kans.

[73] Assignee: Brahler Products, Inc., Lawrence, Kans.

[*] Notice: This patent issued on a continued prosecution application filed under 37 CFR 1.53(d), and is subject to the twenty year patent term provisions of 35 U.S.C. 154(a)(2).

[21] Appl. No.: 09/021,980

[22] Filed: Feb. 11, 1998

[51] Int. Cl.$^7$ ........................................................ A61C 1/12
[52] U.S. Cl. ........................................... 433/125; 433/128
[58] Field of Search ..................... 433/114, 125, 433/126, 128

[56] References Cited

U.S. PATENT DOCUMENTS

| | | | |
|---|---|---|---|
| 3,389,468 | 6/1968 | Lewis et al. ................................ | 433/82 |
| 3,691,636 | 9/1972 | Peuschle .................................... | 433/82 |
| 3,727,313 | 4/1973 | Graham ..................................... | 433/125 |
| 3,740,853 | 6/1973 | Brahler . | |
| 3,798,777 | 3/1974 | Reiter ........................................ | 433/125 |
| 3,858,368 | 1/1975 | Cocherell et al. ....................... | 433/127 |
| 4,266,933 | 5/1981 | Warden et al. . | |
| 4,486,175 | 12/1984 | Fisher et al. . | |
| 5,020,994 | 6/1991 | Huang . | |
| 5,028,233 | 7/1991 | Witherby ................................... | 433/125 |
| 5,040,978 | 8/1991 | Falcon et al. ............................ | 433/125 |
| 5,057,015 | 10/1991 | Fleer ........................................ | 433/126 |
| 5,120,220 | 6/1992 | Butler ....................................... | 433/125 |
| 5,178,538 | 1/1993 | Eckert ...................................... | 433/125 |
| 5,209,658 | 5/1993 | Brahler ..................................... | 433/125 |
| 5,252,067 | 10/1993 | Kakimoto ................................ | 433/126 |
| 5,340,310 | 8/1994 | Bifulk ...................................... | 433/126 |
| 5,380,202 | 1/1995 | Brahler . | |
| 5,496,218 | 3/1996 | Brahler . | |
| 5,692,901 | 12/1997 | Roth et al. ............................... | 433/125 |
| 5,871,353 | 2/1999 | Pierce et al. ............................. | 433/84 |

*Primary Examiner*—Ralph A. Lewis
*Attorney, Agent, or Firm*—Hovey, Williams, Timmons & Collins

[57] ABSTRACT

A dental prophy angle which includes a separate rib for securing each of the drive assembly and a workpiece by a friction lock. Preferably this rib is circumferential and present in both the shank end and the head end of the prophy angle. Each rib of the friction lock will permit the workpiece or the drive assembly to pass by the rib and be inserted into the housing. However, the ribs will not permit the inserted workpiece or drive assembly to pass backwards over the rib and be withdrawn from the housing.

1 Claim, 1 Drawing Sheet

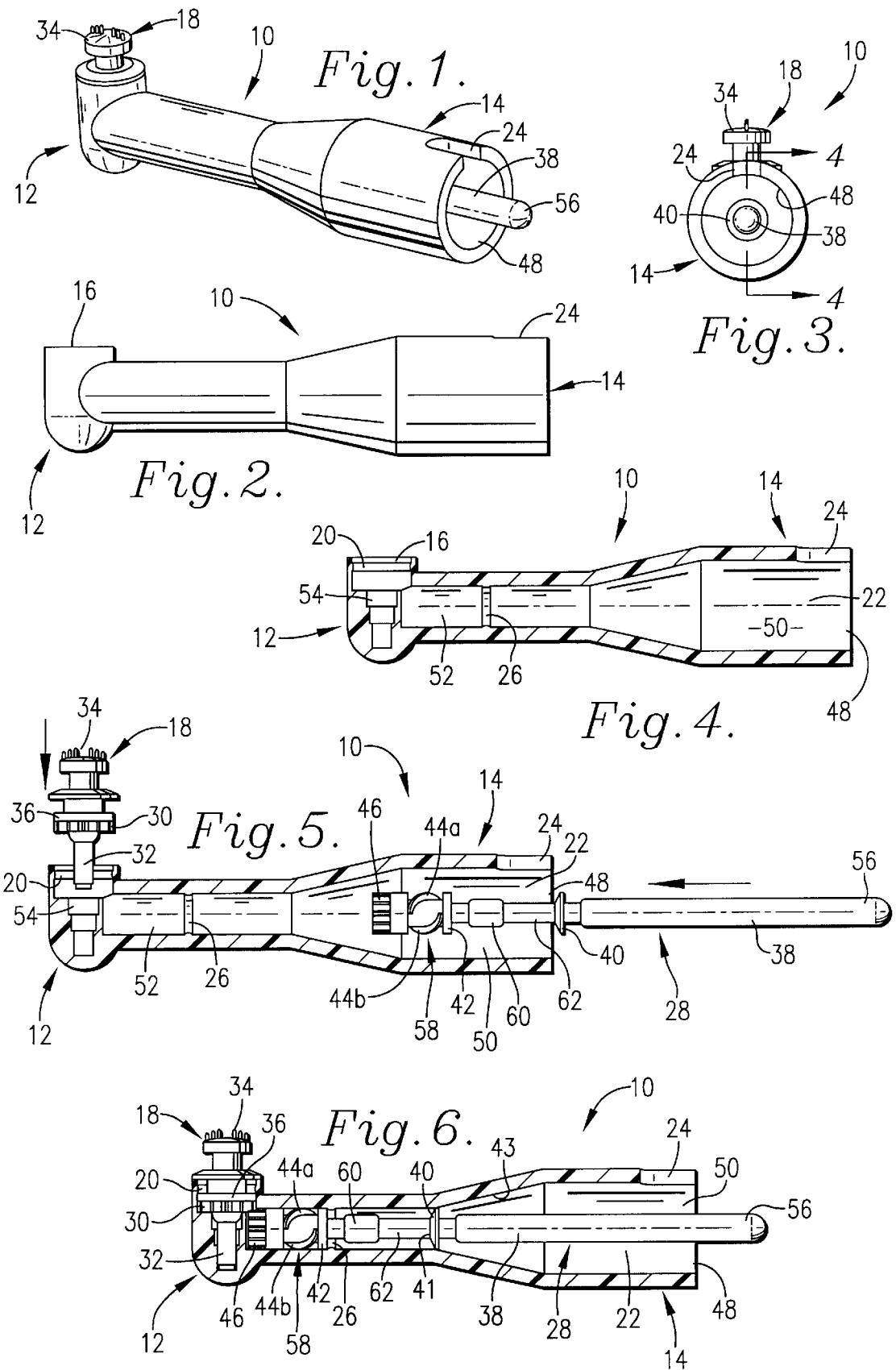

DRIVE SHAFT RETENTION MEANS FOR PROPHY ANGLE

BACKGROUND OF THE INVENTION

1. Field of the Invention

The present invention is concerned with the field of dentistry and specifically with the field of dental prophy angles used for dental prophylaxis. More particularly, the invention is concerned with a dental prophy angle including a housing with a head end containing a rib for locking a workpiece within the head end by way of a friction lock. The housing further includes a shank end and a structure defining a passageway extending between the shank end and the head end with a rib on this structure for locking a drive assembly within the housing by way of a friction lock.

2. Description of the Prior Art

Disposable prophy angles have been used for a number of years. They are generally formed of a suitable synthetic resin material and are designed to be coupled with a conventional dental power supply. Disposable prophy angles are convenient to use and minimize the risk of disease transmittal to the dentist and to patients.

The currently available disposable prophy angles present a particular problem in that they are difficult and time-consuming to manufacture. Because they are made of a plastic, they must be welded together which requires numerous man hours of work. Thus the disposable prophy angles are expensive to make. Furthermore, a plastic weld is not reliable. The connections between the plastic parts often fail during dental work. This wastes time in dental appointments and it poses a risk of injury to both the dentist and the patient. There is a need for a prophy angle which is easy to manufacture and which has secure, stable means for retaining the parts in the desired relationship.

SUMMARY OF THE INVENTION

The present invention solves the problems discussed above by providing a retention means which allows quick manufacturing of the prophy angle. The preferred dental prophy angle includes a housing presenting a head end and a shank end with a structure defining a passageway extending between said ends, a drive shaft extending along the passageway, and a workpiece in the opening of the head end. The workpiece and the drive shaft are each individually secured to the housing by a separate friction lock.

The friction lock consists of a rib on the structure of the housing which permits the workpiece and the drive assembly to pass by the rib when inserted into the housing. The rib will then not permit the workpiece or the drive assembly to be withdrawn from the housing. As no welding is required for this assembly, a person or a machine can quickly assemble this prophy angle by applying pressure to the workpiece and drive assembly until they "pop" over the ribs and into the desired position within the housing of the prophy angle. Furthermore, because there is no welding involved, the risk of the connections failing is greatly minimized.

BRIEF DESCRIPTION OF THE DRAWINGS

FIG. 1 is a perspective view of the preferred dental prophy angle in accordance with the present invention;

FIG. 2 is a side elevational view of the prophy angle;

FIG. 3 is an end elevational view of the shank end of the prophy angle;

FIG. 4 is a sectional view taken along line 4—4 of FIG. 3.

FIG. 5 is a sectional view of the prophy angle illustrating the proper insertion of the drive assembly and the workpiece into the housing.

FIG. 6 is a sectional view of the prophy angle with the drive assembly and workpiece in their retained positions.

DETAILED DESCRIPTION OF THE PREFERRED EMBODIMENT

FIG. 1 shows a dental prophy angle 10, which includes a head end 12 and a shank end 14. Head end 12 of prophy angle 10 has an output opening 16 which receives workpiece 18. Head end 12 includes a first low profile, rounded rib 20 circumferentially positioned on an inner surface of the head end 12 for retaining workpiece 18.

Shank end 14 has a passageway 22, slot 24 (fully shown in FIG. 1), and a second low profile, rounded rib 26. The ribs 20, 26 are bulges extending inwardly from the inner wall of the housing. FIG. 6 illustrates shank end 14 when it includes a drive assembly 28. As shown in FIGS. 5 and 6, prophy angle 10 is an integrally formed housing for receiving workpiece 18 and drive assembly 28. The housing presents a passageway 22 defined at one end by output opening 16 and defined by a first inner surface at the head end 12 and a second inner surface at the shank end 14. The second inner surface connects to the first inner surface adjacent said head end 12. The workpiece 18 has an output gear 30, base 32, working end 34, and first positioning ring 36.

Drive assembly 28 has a drive shaft 38, an annular seal 40, a second positioning ring 42, auger flights 44(a) and 44(b), and a drive gear 46. The annular seal 40 extends outwardly from the drive shaft 38 toward the second inner surface into a close sealing relationship therewith and is positioned rearwardly from the shaft sealing section 60. The annular seal ring includes an inclined front surface 41 which progressively, sealably engages an inclined portion 43 of the inner surface of the shank end 14.

Slot 24 in shank end 14 allows an opening 48 defined at the outer end of shank end 14, to expand for receiving and holding a dental tool drive power source of slightly greater diameter than said shank end opening 48. Passageway 22 of shank end 14 includes power source connection chamber 50, auger chamber 52, and output chamber 54. Output chamber 54 extends transversely relative to auger chamber 52 and opens through head end 12 at output opening 16.

Preferably, components 38-46 of drive assembly 28 are integrally formed of synthetic resin material with the relative positions as shown in FIG. 6. More particularly, drive shaft 38 extends along passageway 22 between auger chamber 52 and power source connection chamber 50 with a rearward portion 56 of drive shaft 38 extending slightly beyond power source connection chamber 50 (as illustrated in FIG. 6).

Drive assembly 28 also includes auger section 58, shaft sealing section 60, an intermediate section 62, and rearward portion 56 of drive shaft 38. Auger section 58, shaft sealing section 60, and rearward portion 56 present diameters slightly greater than intermediate section 62. In this regard, auger section 58 supports integral auger flights 44(a) and 44(b) in auger chamber 52 (as illustrated in FIG. 6). Passageway 22 of shank end 14 could include a plurality of circular sealing rings extending from the housing walls toward the center of passageway 22 and engaged with shaft sealing section 60.

Positioning ring 42 extends around drive shaft 38 adjacent the rearward portions of auger flights 44(a) and 44(b). When the drive assembly 28 is inserted into passageway 22 of shank end 14 in the direction shown in FIG. 5, a small amount of pressure is needed to push the positioning ring 42 beyond rib 26. Once positioning ring 42 is past rib 26 within the forward section of the shank end 14, positioning ring 42 cannot be moved back towards the opening 48 of shank end 14 and the drive assembly is locked in place with a forward end of the drive shaft 38 adjacent said housing head end 12.

Referring to FIG. 6, workpiece 18 is positioned within output opening 16 with the axis thereof transverse to the axis of drive shaft 38. Rib 20 of head end 12 permits second positioning ring 36 of output gear 30 to be pushed into the output opening 16 by applying a small amount of pressure. Once second positioning ring 36 is pushed beyond rib 20, workpiece 18 is locked in place. Base 32 of workpiece 18 along with second positioning ring 36 cooperatively maintains the transverse and axial alignment of workpiece 18 within output opening 16. In this position, output gear 30 engages drive gear 46 for driven rotation thereby. Working end 34 of workpiece 18 can be any of a number of various dental prophylaxis tools.

It will be appreciated that rib 20 could be positioned at various locations within head end 12 and still achieve the desired retention of workpiece 18. Likewise, rib 26 could be positioned at various locations within shank end 14 and still achieve the desired retention of drive assembly 28. Furthermore, it is foreseeable that one skilled in the art could choose to use the rib in either head end 12 or shank end 14 rather than both head end 12 and shank end 14.

In use, a dental drive power source is inserted into opening 48 of shank end 14 and slipped over rearward portion 56. The power source is pressure fitted within slot 24 for holding the power source engaged with drive shaft 38. A prophylaxis tool is then coupled with head end 12 and the power source is activated to rotate drive shaft 38 which in turn rotates drive gear 46 and thereby rotates output gear 30 and the prophylaxis tool (working end 34).

Rotation of drive shaft 38 also rotates auger flights 44(a) and 44(b) which propels buccal matter forward and expels this buccal matter from prophy angle 10 through output opening 16. When the dental power source is turned off and auger flights 44(a) and 44(b) are not rotating, small amounts of buccal matter may migrate beyond flights 44(a) and 44(b). This migration is prevented by annular seal 40 engaged with shaft rearward portion 56.

As those skilled in the art will appreciate, the present invention encompasses many variations of the preferred embodiment described herein. For example, in some circumstances one auger flight will be sufficient and could be positioned at a different location along the prophy angle passageway. Additionally, the preferred prophy angle presents an output transverse to the long axis, which could be positioned at some other relative orientation. Furthermore, a plurality of seals could be utilized to prevent the migration of buccal matter towards the dentist's handpiece. Finally, the number and location of the ribs can be varied and still achieve the object of this invention.

What is claimed is:

1. A dental prophy angle comprising:

an integrally formed housing presenting a head end and a shank end with a passageway extending through said housing between said ends, said head end having an opening that defines one end of said passageway, the shank end having an opening which defines the other end of the passageway, a head end inner surface defining a portion of said passageway;

a first rib integral with said head end inner surface, adjacent said head end opening, said first rib being low profile and having an innermost rounded edge spaced slightly from the head end inner surface;

a workpiece inserted in said head end opening through said one end of the passageway;

a first positioning ring carried by the workpiece and movable through said head end opening beyond the first rib into the one end of the passageway to permit the rib to engage the ring and thereby retain the workpiece in the head end;

a shank end inner surface in the passageway;

a second low profile rib extending inwardly from said shank end inner surface, integral therewith and intermediate the ends thereof;

a drive assembly inserted in the other end of the passageway and including a drive shaft extending along said shank end passageway, said drive shaft including a rearward portion for coupling a dental handpiece thereto; and a second positioning ring integral with the drive shaft and extending radially outwardly therefrom and movable beyond said second rib in the shank end passageway to permit the second rib to engage the second positioning ring to thereby retain the drive assembly in the shank end of the passageway.

* * * * *